US012806252B2

(12) United States Patent
Balu-Iyer et al.

(10) Patent No.: US 12,806,252 B2
(45) Date of Patent: Nov. 24, 2026

(54) COMPOSITIONS AND METHODS FOR USE IN TYPE 1 DIABETES

(71) Applicant: The Research Foundation for The State University of New York, Amherst, NY (US)

(72) Inventors: Sathy V. Balu-Iyer, Amherst, NY (US); Vincent Chak, Amherst, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 1122 days.

(21) Appl. No.: 17/779,072

(22) PCT Filed: Nov. 23, 2020

(86) PCT No.: PCT/US2020/061859
§ 371 (c)(1),
(2) Date: May 23, 2022

(87) PCT Pub. No.: WO2021/102433
PCT Pub. Date: May 27, 2021

(65) Prior Publication Data

US 2022/0409702 A1 Dec. 29, 2022

Related U.S. Application Data

(60) Provisional application No. 63/019,716, filed on May 4, 2020, provisional application No. 62/939,224, filed on Nov. 22, 2019.

(51) Int. Cl.

| | |
|---|---|
| ***A61K 38/00*** | (2006.01) |
| ***A61K 9/1271*** | (2025.01) |
| ***A61K 38/28*** | (2006.01) |
| ***A61K 47/54*** | (2017.01) |
| ***A61P 3/10*** | (2006.01) |

(52) U.S. Cl.
CPC ............ *A61K 38/28* (2013.01); *A61K 9/1271* (2013.01); *A61K 47/544* (2017.08); *A61P 3/10* (2018.01)

(58) Field of Classification Search
CPC .... A61K 38/28; A61K 9/1271; A61K 47/544; A61K 2039/542; A61K 39/0008; A61K 2039/55555; A61P 3/10
See application file for complete search history.

(56) References Cited

U.S. PATENT DOCUMENTS

| | | | | |
|---|---|---|---|---|
| 2003/0068361 | A1 | 4/2003 | Margalit | |
| 2016/0338953 | A1 | 11/2016 | Maspoch et al. | |
| 2017/0209371 | A1* | 7/2017 | Balu-Iyer ........... | A61K 38/1709 |

FOREIGN PATENT DOCUMENTS

| | | | |
|---|---|---|---|
| WO | 98/43616 | A1 | 10/1998 |
| WO | 03/30829 | A2 | 4/2003 |
| WO | 2012/088414 | A1 | 6/2012 |
| WO | 2012/161856 | A1 | 11/2012 |
| WO | 2014/004866 | A1 | 1/2014 |
| WO | 2017/176916 | A1 | 10/2017 |
| WO | 2017/190145 | A1 | 11/2017 |

OTHER PUBLICATIONS

Kim et al. (Mol Pharm. Oct. 1, 2018; 15(10): 4756-4763).*
Bonifacio et al. (JAMA. 2015;313(15):1541-1549).*
Beik et al. Prevention of Type 1 Diabetes: Past Experiences and Future Opportunities, 2020, J. Clin. Med. 2020, 9, 2805.*
Jacobsen et al. Frontiers in Endocrinology, 2018, vol. 9, No. 70.*
Glassman et al., "Subcutaneous Administration of Lyso-Phosphatidylserine Nanoparticles Induces Immunological Tolerance Towards Factor VIII in a Hemophilia a Mouse Model," International Journal of Pharmaceutics, Sep. 5, 2018, pp. 642-648, vol. 548, No. 1.
Rimmerman et al., "Insulin Hexamer Dissociation Dynamics Revealed by Photoinduced T-jumps and Time-Resolved X-Ray Solution Scattering," Photochemical and Photobiological Sciences, Jul. 11, 2018, pp. 874-882, vol. 17, No. 7.

* cited by examiner

*Primary Examiner* — Jeanette M Lieb
(74) *Attorney, Agent, or Firm* — Hodgson Russ LLP

(57) ABSTRACT

Provided are methods for preventing, treating, suppressing type 1 diabetes, or reversing one or more symptoms of T1D, or delaying the onset of T1D comprising administration to a subject a composition comprising liposomes and insulin intercalated in the bilayer of the liposomes, wherein the bilayer comprises lyso-PS.

13 Claims, 11 Drawing Sheets

Table 1

Figures 1, 2:
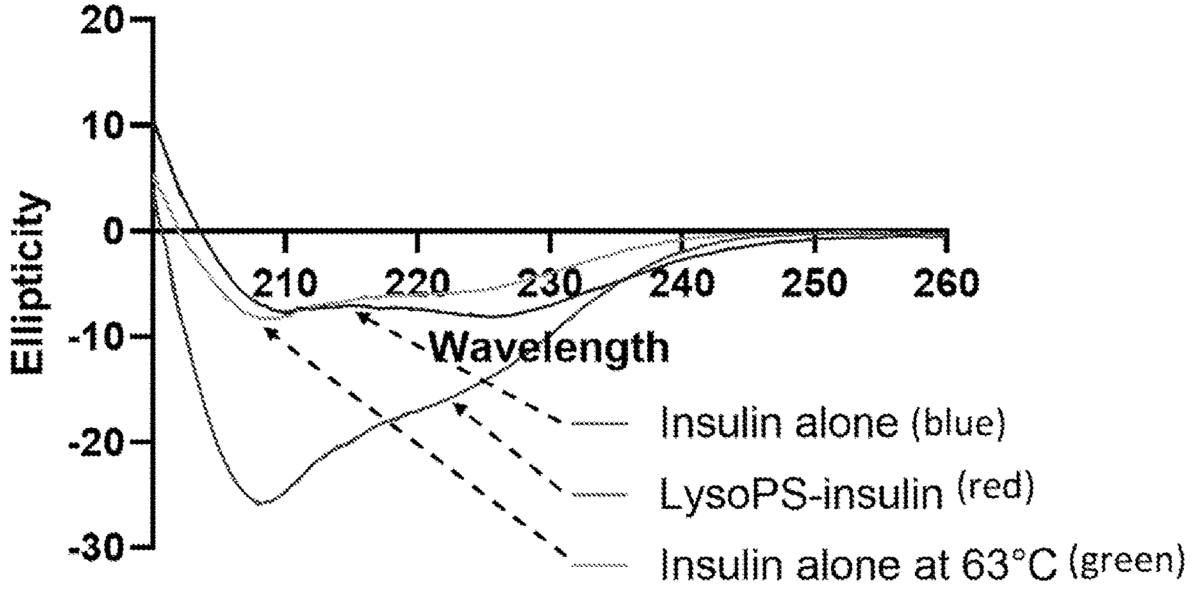

| | Lyso-PS in Tris buffer | Lyso-PS Citrate Buffer |
|---|---|---|
| | % Insulin associated liposome | % Insulin associated liposome |
| Trial 1 | 11.86 | 86.82 |
| Trial 2 | 7.54 | 80.42 |
| Trial 3 | 9.18 | 94.61 |
| Mean | 9.53 | 87.28 |
| SD | 2.18 | 7.11 |

Table 2

| Groups | Diameter (nm) | Polydispersity (pdi) | Zeta potential (mV) |
|---|---|---|---|
| LysoPS alone | 61.1±1.96 | 0.18±0.02 | -24.62±4.88 |
| LysoPS-insulin | 93.6±20.24* | 0.32±0.06 | -24.86±0.38 |

(a) (continued)

COMPOSITIONS AND METHODS FOR USE IN TYPE 1 DIABETES

CROSS-REFERENCE TO RELATED APPLICATIONS

This application claims priority to U.S. Provisional patent application No. 62/939,224, filed on Nov. 22, 2019, and to U.S. Provisional patent application No. 63/019,716, filed on May 4, 2020, the disclosures of which are incorporated herein by reference.

STATEMENT REGARDING FEDERALLY SPONSORED RESEARCH

This invention was made with government support under contract no. HL070227 awarded by the National Institutes of Health. The government has certain rights in the invention.

BACKGROUND OF THE DISCLOSURE

Type 1 diabetes (T1D) is a chronic cell-mediated autoimmune disease where insulin-producing β-cells in the islets of Langerhans are destroyed as a result of chronic inflammation, resulting in hypoinsulinemia and inability to maintain glucose homeostasis. Despite the large population of patients suffering from T1D, treatment options are limited. Factors responsible for T1D are complex and considered to involve a combination of genetic, environmental, and immunologic influences. While multiple antigens have been implicated in T1D, including insulin, proinsulin, 65 kDa glutamic acid decarboxylase (GAD65; also known as glutamate decarboxylase 2), insulinoma-associated protein 2 (IA2) or zinc transporter 8 (ZNT8), insulin is recognized as a major factor and abnormally elevated immune response toward insulin is one of the suspected causes of T1D.

The progression of type 1 diabetes prior to clinical presentation has been extensively studied in search of clues to the etiology and pathogenesis of beta cell destruction. The prediabetic period may span only a few months (e.g., in very young children) to years (e.g., older children and adults). The earliest evidence of beta cell autoimmunity is the appearance of various islet autoantibodies. Metabolically, the onset of diabetes may be observed through intravenous glucose tolerance testing (IVGTT) or oral glucose tolerance test (OGTT).

A current clinical treatment for T1D patients is to administer recombinant human insulin as replacement therapy along with restriction of diet. However, the replacement therapy is initiated only after a diagnosis of T1D. Currently, there is no method for delaying the onset of the disease. Moreover, no cure has been developed. As a result, patients may have to receive life-long exogenous insulin in order to maintain normal cellular metabolism. As such, there is a continuing need to develop new strategies to delay onset, treat, manage or reverse T1D.

SUMMARY OF THE DISCLOSURE

The present disclosure provides compositions and methods for delaying or arresting the onset of, treatment, prevention, suppressing and/or reversing type 1 diabetes.

The compositions comprise insulin associated with liposomes. The term "liposomes" is used interchangeably with "lipid nanoparticles" or "lipid particles" or "lipidic nanoparticles" or "lipidic particles". The liposomes comprise phosphatidylcholine (PC) and phosphatidylserine (PS), wherein some or all of the PS may be present as lysophosphatidylserine (lyso-PS). In an embodiment, all of the PS may be present as lyso-PS.

The acyl chain length for lyso-PS may be 16, 18 or 20 with one or more double bonds. The acyl chain length of the PC chains can be from 12-22. The PC may be DMPC. As an example, the present disclosure provides liposomes which comprise PC and PS, all the PS being present as lyso-PS, wherein the molar ratio of PC to lyso-PS is from 90:10 to 10:90. The ratio of PC to lyso-PS may be from 40:60 to 60:40. The acyl chain of the lyso-PS can contain from 16 to 20 carbons. It was observed that a chain length of 18 with one double bond (18:1, oleic acid) was particularly effective in delaying onset of diabetes and treatment of diabetes in a T1D animal model. The liposomes comprising lyso-PS may be referred to herein as lyso-PS liposomes.

Insulin can be loaded on to the liposomes by using a trigger loading method where an elevated temperature is used to bring about a conformation change, such as, unfold the insulin, the unfolded insulin is then incubated with the lyso-PS liposomes and after a period of time, the liposomes are allowed to return to room temperature which results in intercalation of at least a part of the insulin within the liposomal bilayers. The altered conformational states can be generated with lower pH (for e.g., 5-6) in combination with elevated temperature (such as up to 70 C). The insulin-liposomal complex is referred to herein as "insulin-lysoPS liposomes" or "insulin-lysoPS particles" or "insulin-lysoPS nanoparticles" (or other similar terms) or simply "lysoPS-insulin". In these forms, insulin is referred to as being associated with the liposomes or complexed with the liposomes. Part of the insulin molecule may be intercalated in the bilayer, in the lumen, surface exposed or a combination of these configurations.

The insulin-lyso PS liposome composition may be administered as needed to a subject in need of treatment in connection with T1D.

BRIEF DESCRIPTION OF THE FIGURES AND TABLES

FIG. 1: Table 1: Association efficiency of LysoPS-insulin nanoparticles. LysoPS-insulin Association Efficiency measured by size exclusion chromatography. This table shows results of three independent runs. Table 2: Particle size of LysoPS-insulin nanoparticle. Size and Zeta potential were measured for both LysoPS lipid nanoparticles and LysoPS-insulin lipid nanoparticles using dynamic light scattering technique. Two-tailed paired student t test performed and $P<0.05$ considered as statistically significant.

FIG. 2: Far-UV spectrum of LysoPS-insulin lipid nanoparticle. Far-UV Circular Dichroism spectrum showing the secondary structural features of insulin alone (blue), insulin alone incubated at 63° C. (green), (background corrected with buffer). LysoPS-insulin group (red) (background subtracted with unloaded LysoPS liposome). Experiments were performed in triplicate.

Figure 3:
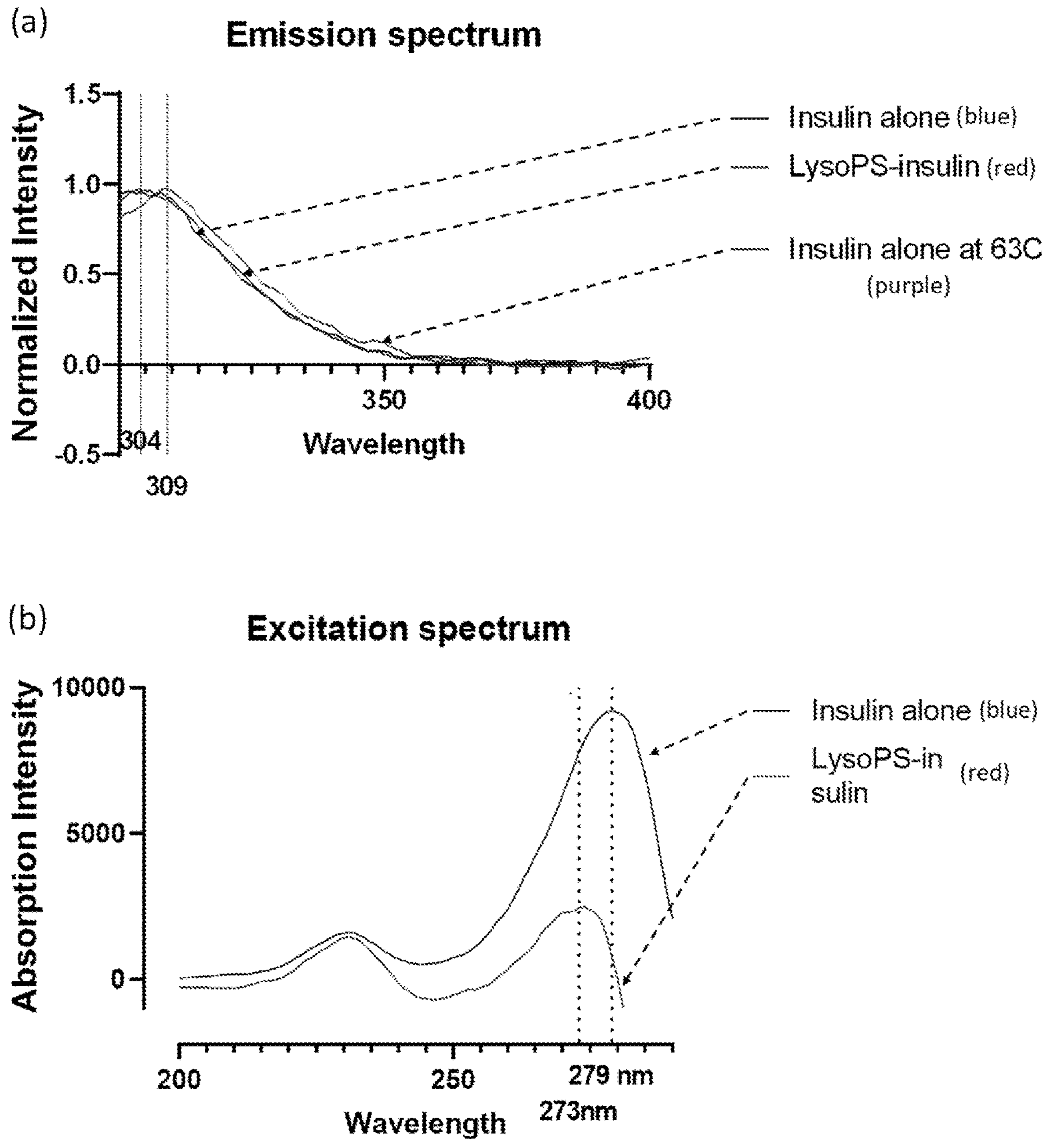

FIG. 3: Fluorescence emission and excitation spectrum. In FIG. 3*a*, steady state fluorescence emission spectra; insulin alone (blue) LysoPS-insulin (red) and insulin alone at 63° C. (purple). In FIG. 3*b*, excitation spectra of insulin alone (blue) and LysoPS-insulin(red) are shown and were collected between 200 nm to 285 nm with emission monochromator set at tyrosine emission of 304 nm. Light scattering from both figures were background subtracted with buffer or unloaded liposome alone and experiments were performed in triplicate.

Figure 4:
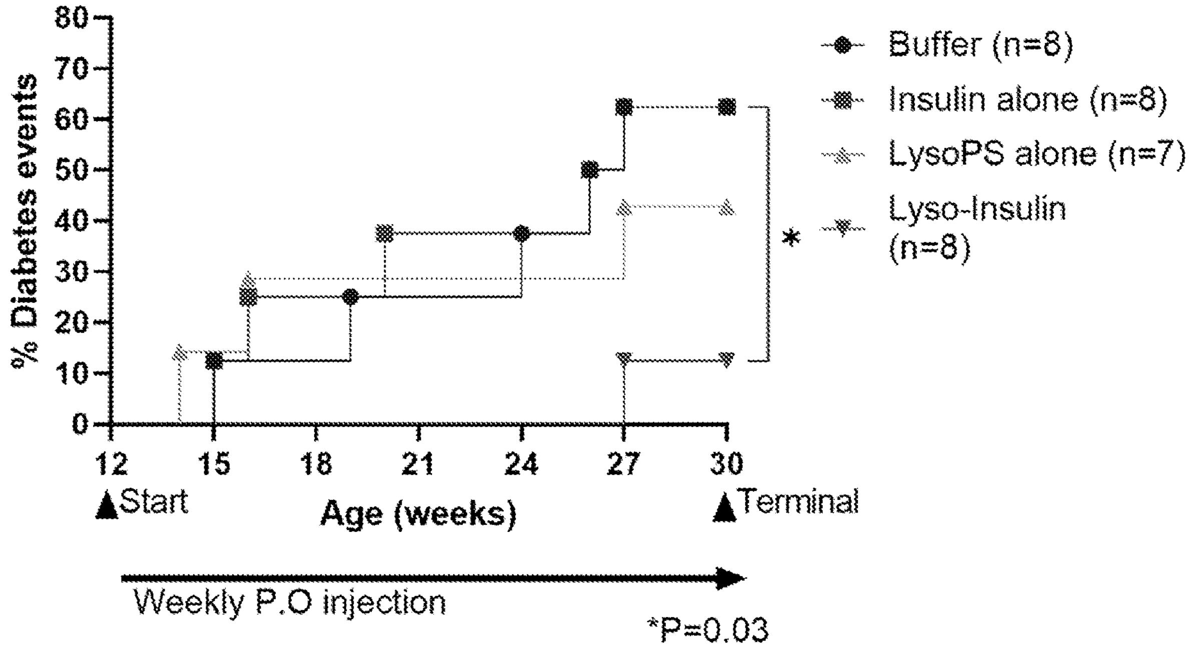

FIG. 4: Immunotherapy using LysoPS-insulin lipid nanoparticle decrease incidence of T1D. Diabetes incidence is defined as glucose level of 250 mg/dL for two consecutive days. Mice from all treatment groups were individually monitored and their glucose levels were measured weekly. Cumulative incidence (Percentage) of T1D in non-obese diabetic (NOD) mice treated with Buffer (filled circle n=8), insulin alone (square n=8), free, unloaded LysoPS lipid nanoparticle (triangle up n=7) and insulin loaded LysoPS lipid nanoparticle (triangle down n=8). Significant differences were found when glucose levels were compared between Buffer versus LysoPS-insulin and insulin alone versus LysoPS-insulin (* P≤0.05, Survival analysis Kaplan-Meier log rank test).

Figure 5:
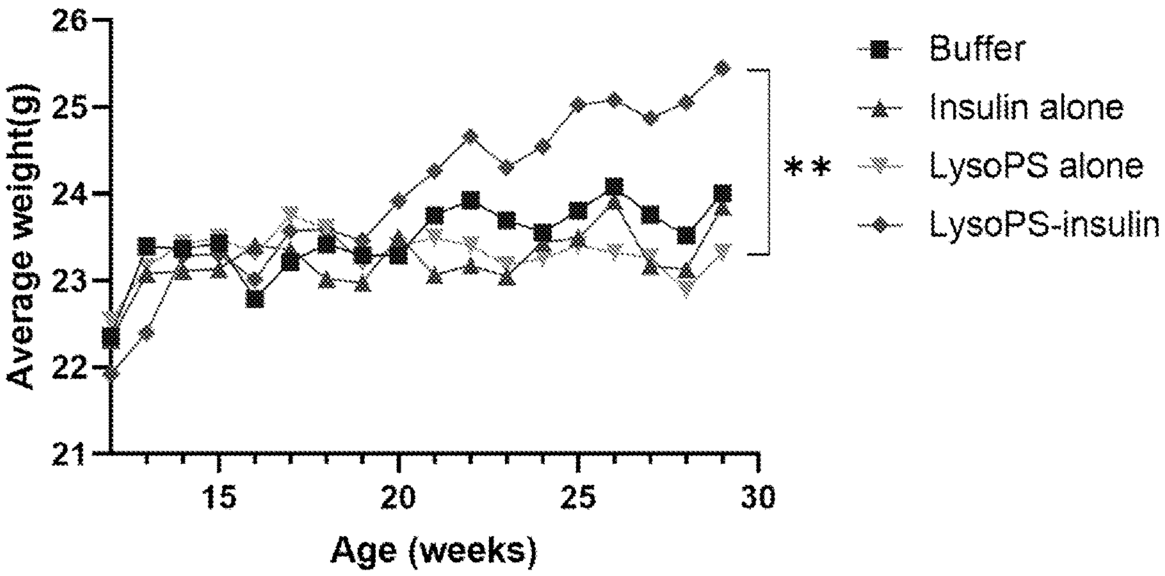

FIG. 5: Administration of LysoPS-insulin lipid nanoparticle maintains normal body weight in NOD mice. Average weight from each group were compared weekly and disease progression were monitored. Significance was determined at the $p<0.05$ level using Kruskal-Wallis test with Dunn's multiple comparison's test.

Figure 6:
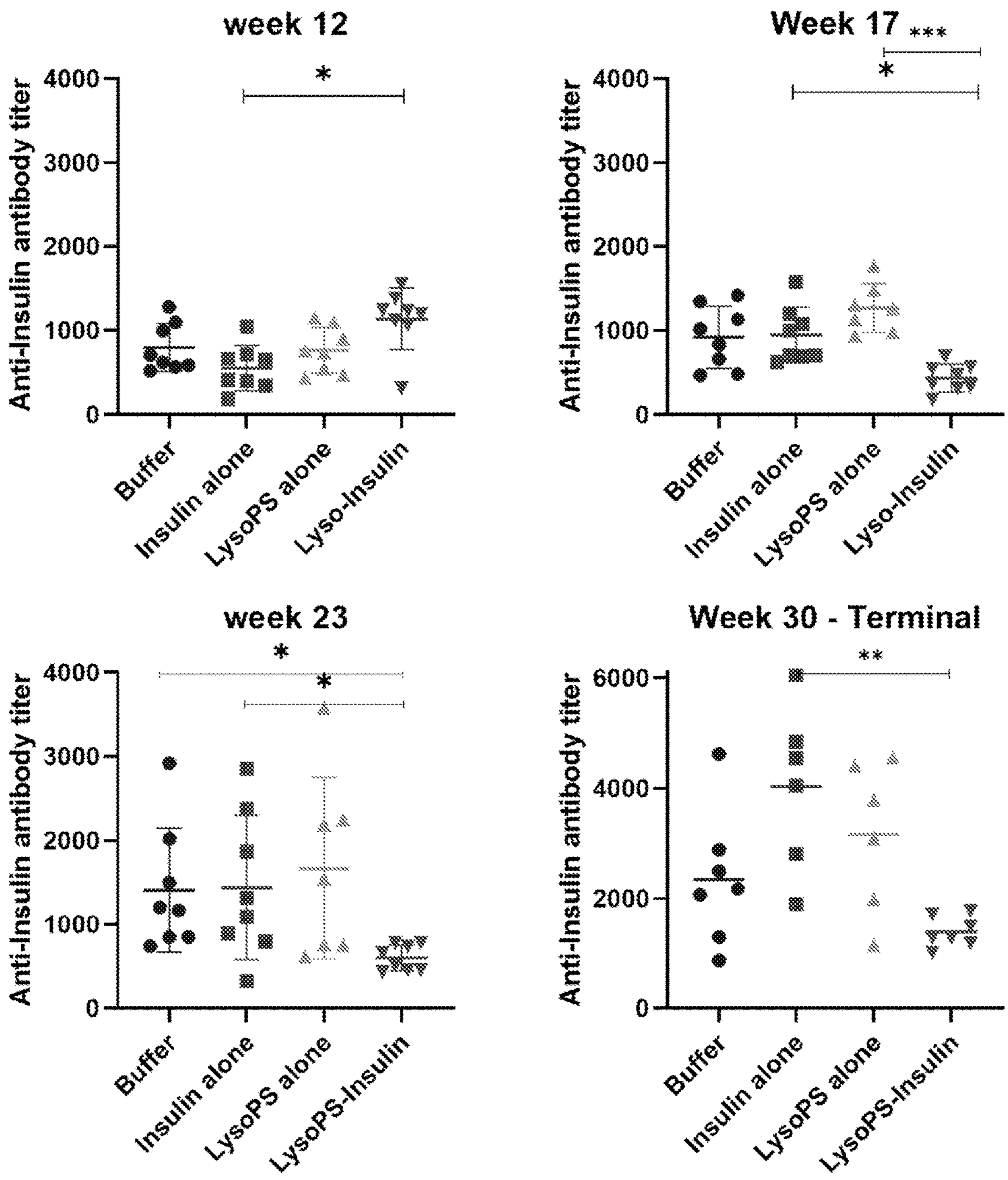

FIG. 6: LysoPS-Insulin administration lowers anti-insulin antibody development. Plasma samples were analyzed and each data point represents one animal and the bar represents mean±SD. Data included early euthanasia of NOD mice for comparison. Significance was determined at the $p<0.05$ level using Kruskal-Wallis test with Dunn's multiple comparison's test.

Figure 7:
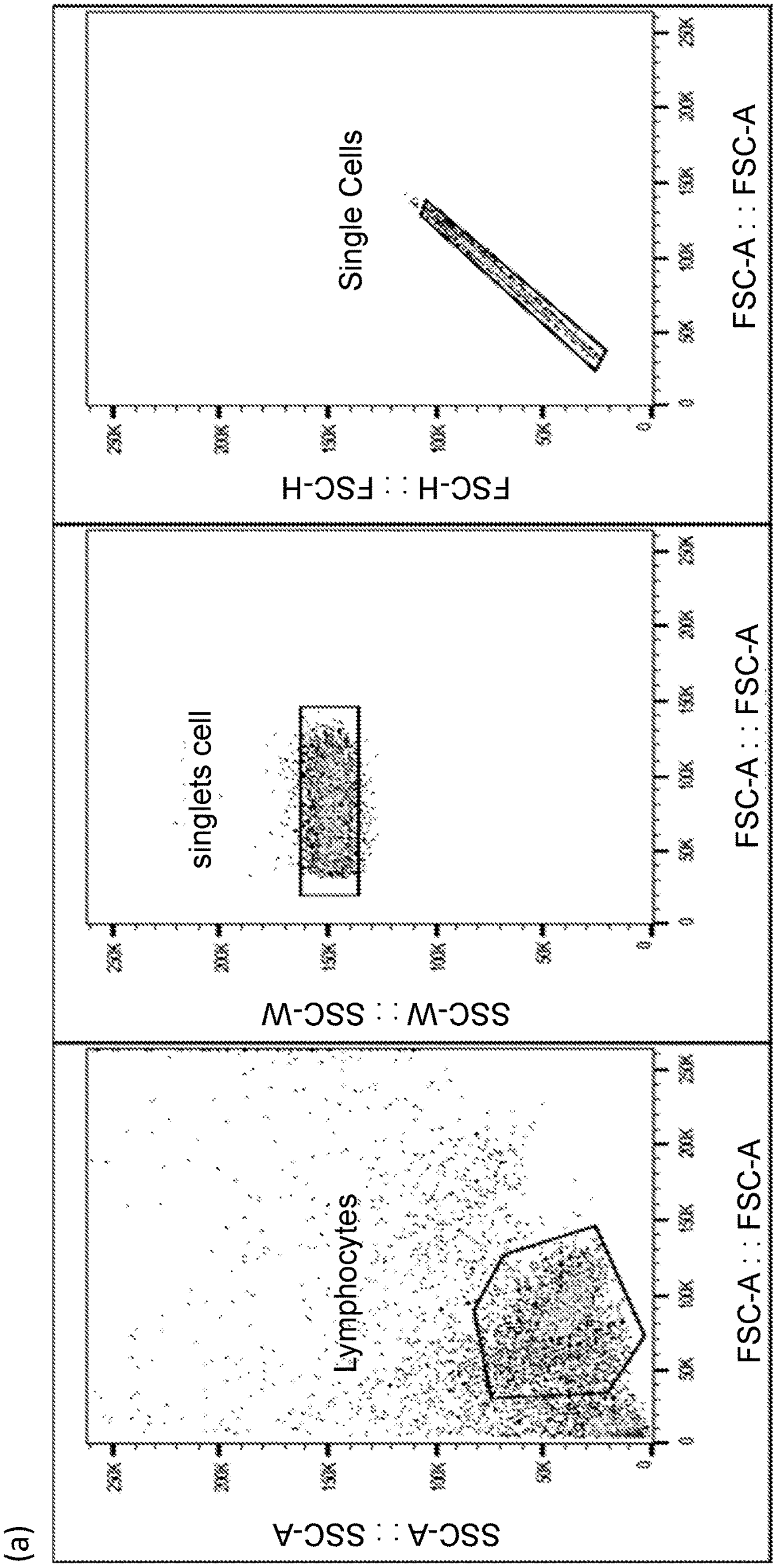
Figure 7:
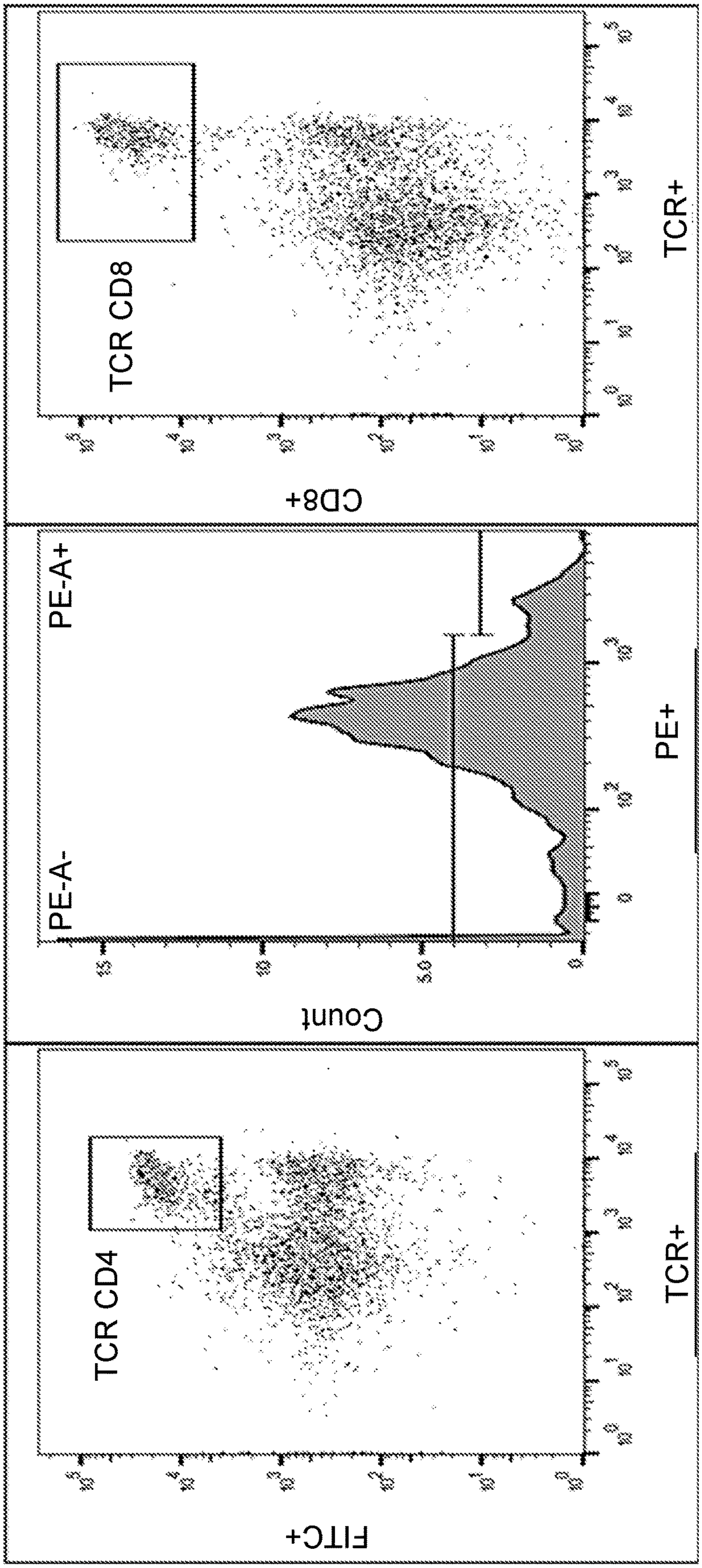
Figure 7:
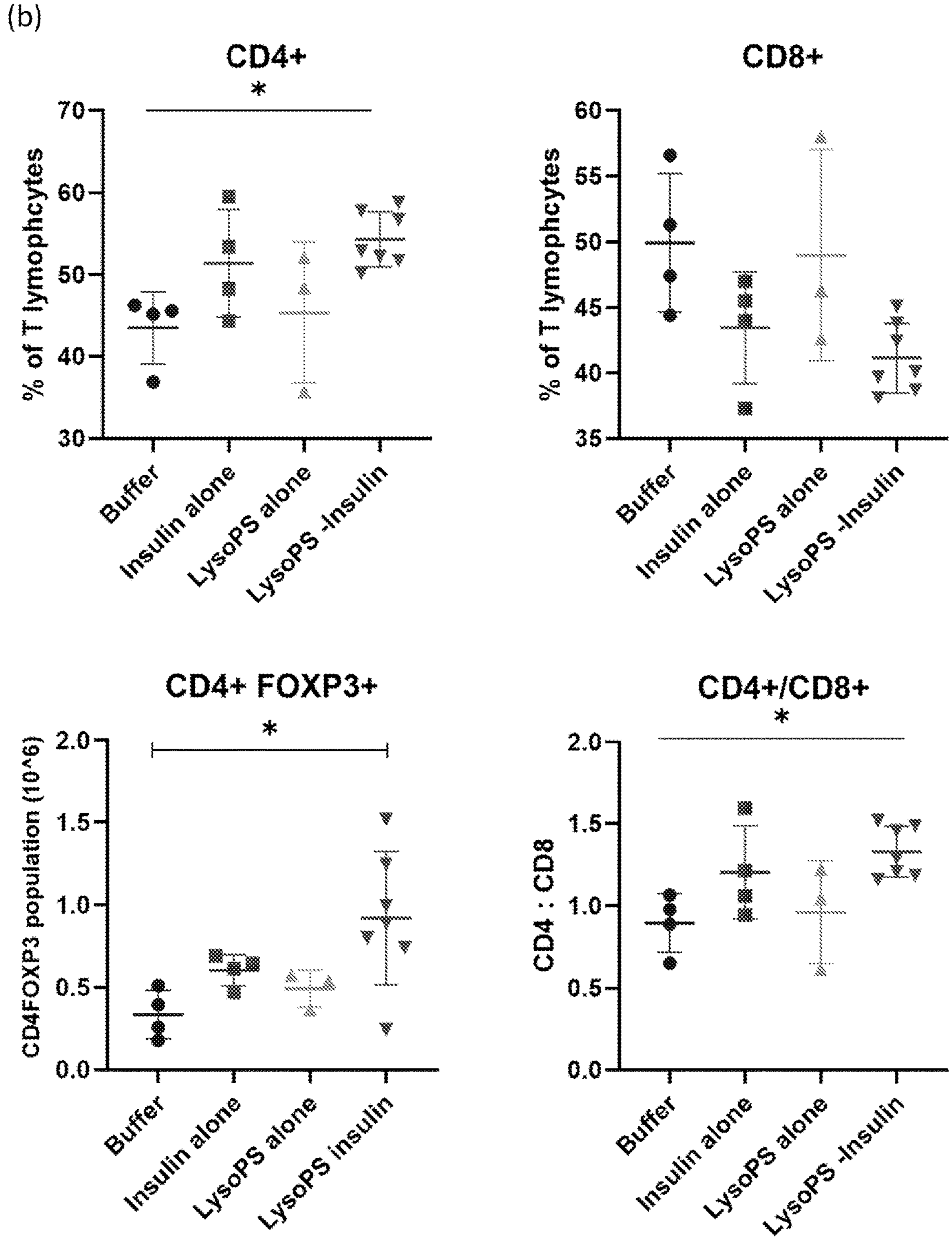

FIG. 7: LysoPS-Insulin administration induces expanding of CD4+ T cells and increase regulatory T cells expansion. (a) Gating protocol to analyze sub-population of T cells identified through staining with CD4+-FITC and CD8+-APC antibody and Regulatory T cell population by staining CD4+-FITC with FOXP3+-PE out of the total T cell population. To reduce overlap between FITC and PE, compensation method was used. (b) The percentage of CD4+ FOXP3+ regulatory T cells and CD8+ cytotoxic T cells that were analyzed using Miltenyi biotech analyzer 10 flow cytometry. Data are represented as mean±SEM and statistical comparison was done using Kruskal-Wallis test with Dunn's multiple comparison's test.

Figure 8:
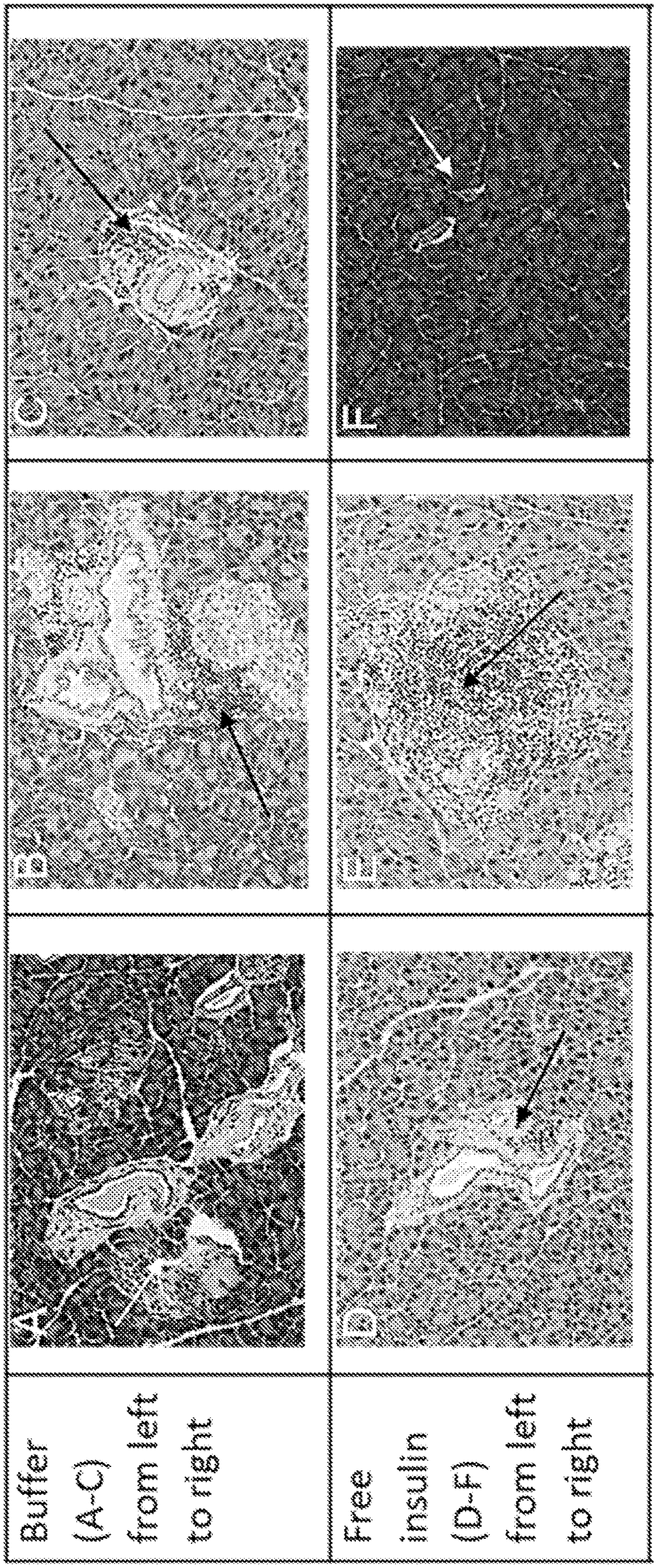
Figure 8:
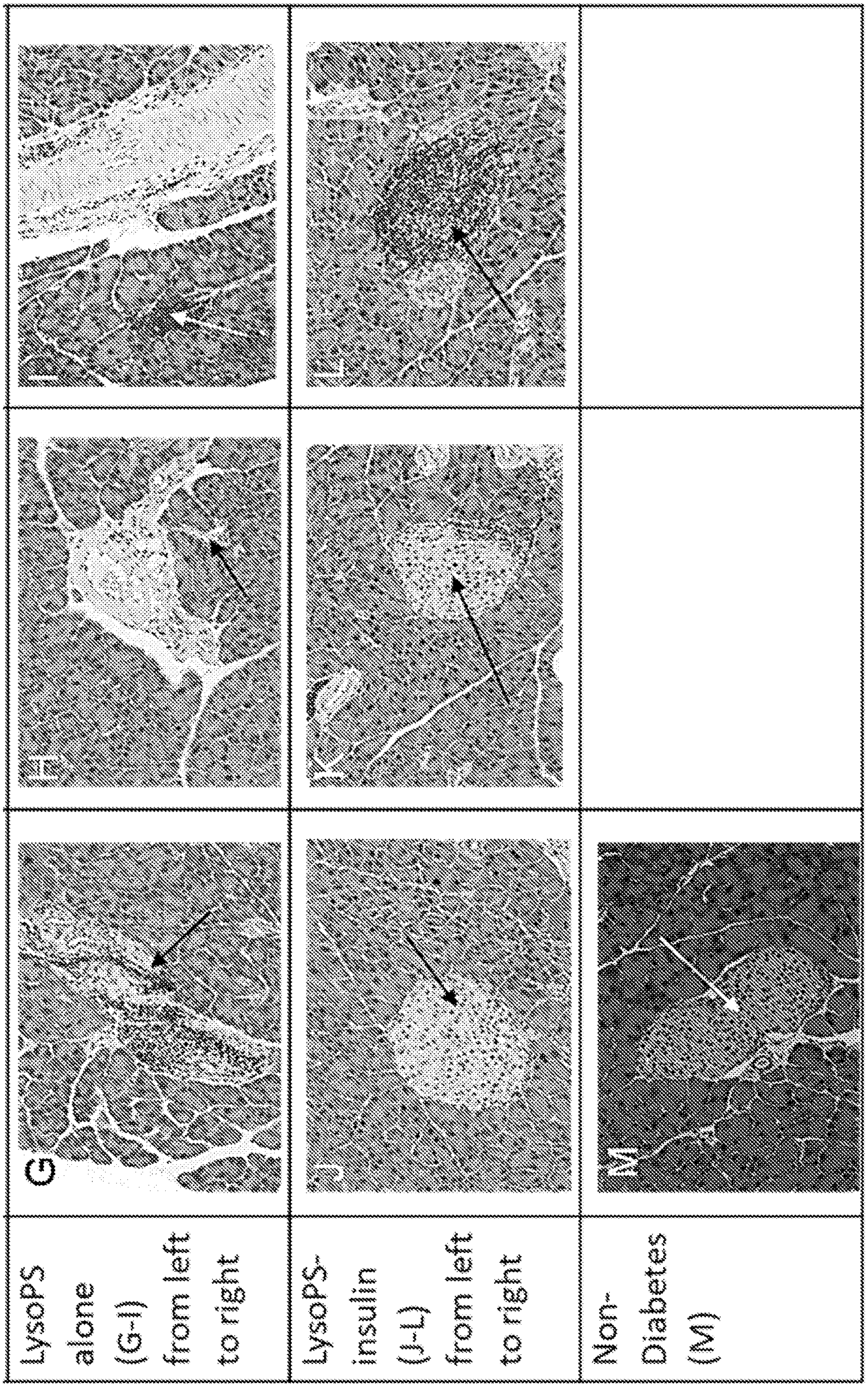

FIG. 8: Pancreas histology (A-M). Pancreas obtained from NOD mice at the end of study, 3 mice from each group were stained with H&E staining. Section of pancreas were captured using confocal microscopy at 200× magnification. Islets cell are indicated with arrow.

Figure 9:
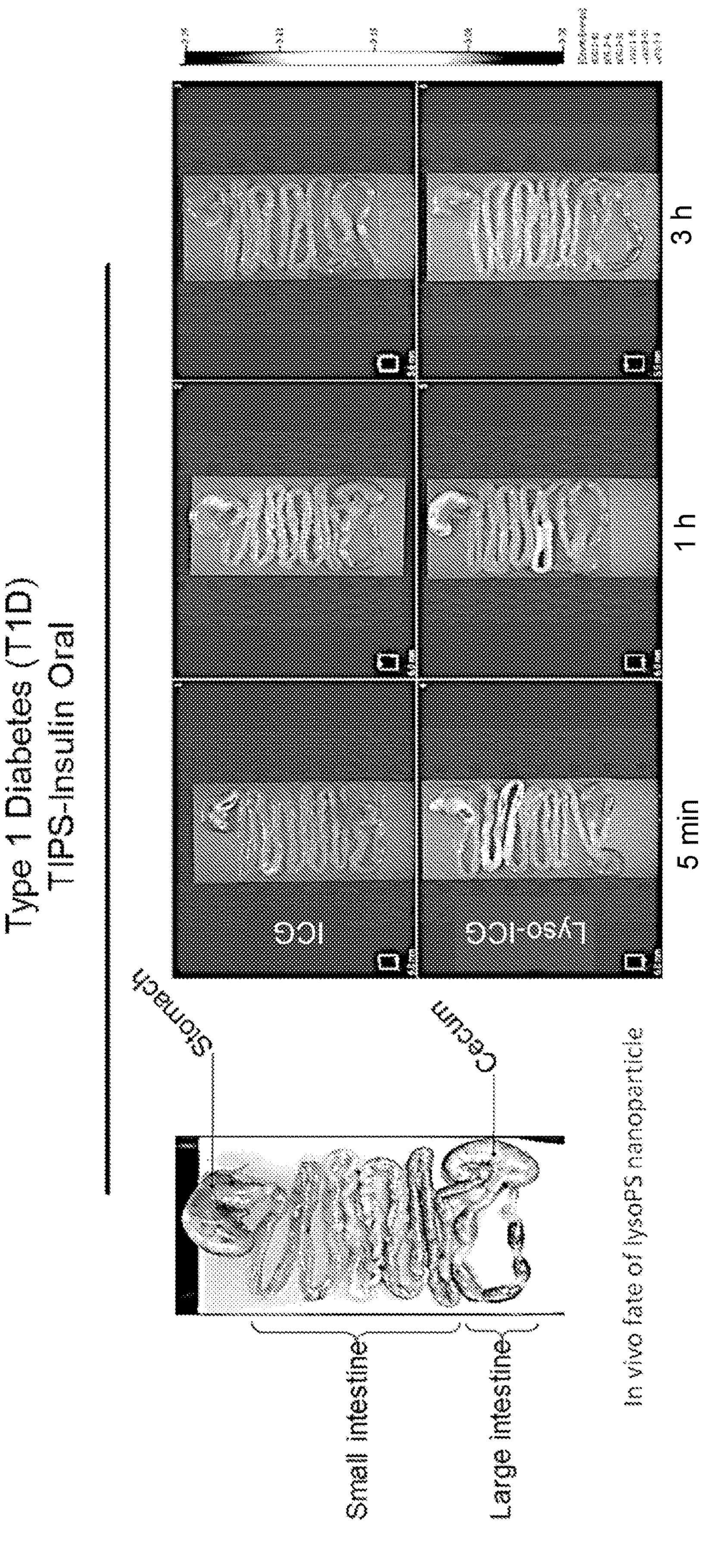

FIG. 9: in vivo stability of Indocyanine green (ICG) labeled lysoPS after oral administration; Top, ICG alone and bottom: lysoPS-ICG.

Figure 10:
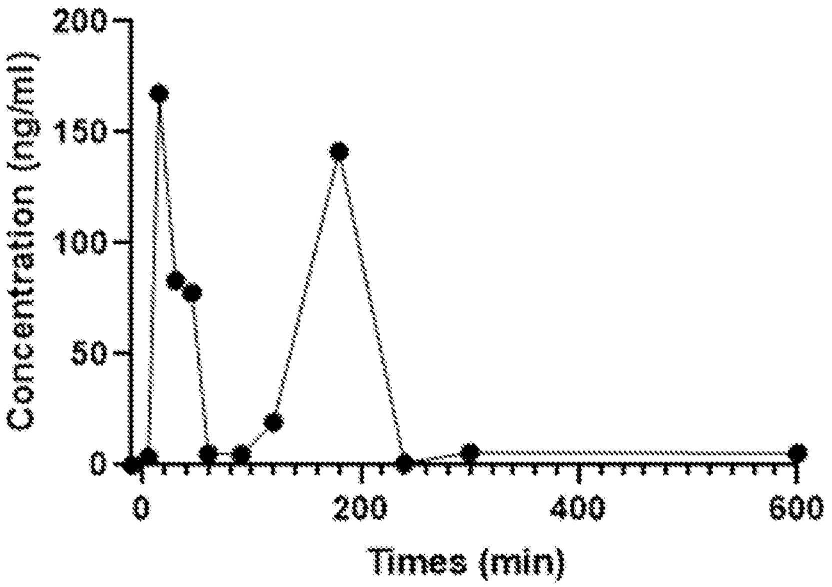

FIG. 10: Pharmacokinetic analysis of LysoPS-insulin in 3 Streptozotocin STZ-induced rats (200 g-300 g) following oral administration.

DETAILED DESCRIPTION OF THE DISCLOSURE

The present disclosure provides methods, compounds and compositions for treating, preventing, suppressing, delaying the onset, reducing the risk of developing type 1 diabetes or the symptoms associated with, or related to, Type 1 diabetes, or reversing the symptoms of Type 1 diabetes in a subject in need thereof.

In the present disclosure, a method is provided for preparing insulin associated with LysoPS liposomes with high association efficiency. An animal model, the non-obese diabetic (NOD) mouse was used to evaluate its use in T1D. The NOD mouse develops a spontaneous type 1 diabetes that shares many of the features associated with human T1D providing a well characterized animal model for this complex autoimmune disease. In the NOD animal model where onset of T1D can be followed, we observed that administration of insulin-lyso-PS liposomes delayed the onset of T1D, and administration to animals that had developed T1D, the clinical condition was improved. The treatment results in downregulated anti-insulin antibody production as well as generation of regulatory T cells. Histology of pancreas tissue also improved with lysoPS-insulin treatment.

As used herein, the term insulin-lysoPS (or lyso-PS-insulin) liposomes means the insulin is complexed/associated to liposomes containing PS and PC, wherein at least some of the PS is lyso-PS. Sometimes the term may be used simply as lysoPS-insulin (without the term liposomes or particles or nanoparticles), but is intended to mean insulin complexed or associated with liposomes comprising lysoPS and PC.

By "lipidic structures" is meant liposomes and other structures such as micellar structures, liposomes, cochleates, molecular assemblies and the like.

The term "lyso" when used herein in conjunction with a phospholipid means that the glycerol part of the molecule has only one acyl chain instead of two. For example, lyso-PS has only one acyl chain as compared to PS which has two acyl chains.

Liposomes are also referred to herein as lipidic nanoparticles, or nanoparticles. The phospholipids for preparing the liposomes can be obtained from any available source such as plant or animal. The phospholipids are commercially available or can be synthesized by known methods. For example, PS can be obtained from porcine brain PS or plant-based soy (e.g., soya bean) PS. Lyso-PS is also available commercially.

The liposomes may comprise PC and PS, wherein some or all PS is in the form of lyso-PS. The liposomes may contain PS, lyso-PS and PC as the only phospholipids. The liposomes may contain lyso-PS and PC as the only phospholipids. The PS or lyso-PS may be in a range of from 10% to 30% molar ratio of the total phospholipids in the bilayer with the remaining phospholipids being mainly PC or only PC. For example, the lyso-PS can be from 10 to 50%, or 15 to 50%, or 15 to 30% (molar), the remaining phospholipids being PC. The liposomes may have PC:lyso-PS as 90:10, 80:20, 70:30, 60:40, or 50:50 molar ratios Only the PS (some or all) is in the form of lyso-PS, while all of PC has two acyl chains. In an embodiment, phosphatidylethanolamine (PE) may be added. PE may be added at the expense of PC up to 20 mol %. The liposomes of lipidic particles may not contain any PG. In an embodiment, there is no PG in the lipid particles. Insulin may be associated with liposomes in multiple configurations. For example, some part of insulin may be intercalated in the bilayer, on the surface or encapsulated (present in the aqueous compartment) in the liposome. Insulin can be in monomeric form, dimeric or multimeric (e.g., hexamer) form.

In one example, the liposomes may further comprise retinoid acid and/or rapamycin. Thus, the liposomes can comprise PS (some or all of which can be lyso-PS), PC and retinoid acid and/or rapamycin. The amount of retinoic acid can be from 0.1 mol % to 10 mol % and all percentage values to the tenth decimal place therebetween. The amount of rapamycin can be 0.1 mol % to 10 mol % and all percentage values to the tenth decimal place therebetween.

PC may have acyl chain length from 14 to 22 carbons (and all integer number of carbons and ranges therebetween). The acyl chain for lyso PS may have from 16 to 20 carbons. It should have at least one double bond. For example, it can be 18:1 (oleic). It may have 2 or 3 double bonds, although the stability of the liposomes was found to be the better with a single double bond than with 2 or 3 double bonds. However, at least one double bond was found to be necessary for enhanced effectiveness. The PC may not be lyso-PC. For example, the PC:PS ratio is 90:10 to 60:40 (molar ratio), and all of the PS is lyso-PS. In an example, the PC:lyso PS may be 85:15 to 65:35. In an example, the ratio of PC:lyso-PS may be 70:30 (molar ratio). In an example, the lyso-PS is from 15 to 50% or 15 to 35% with the remaining phospholipids being PC. The lyso-PS and PC may be the only phospholipids present in the bilayer of the liposomes. In an embodiment, the lyso-PS can be up to 90% of the total phospholipids, with the remaining being PC, or in some embodiments, some of the PC may be replaced with PE.

The loading of insulin on to liposomes can be carried out by trigger loading technique as described in the examples. As a first step, conformationally altered state is generated by increase in temperature and/or decrease in pH. Insulin can be loaded on to the liposomes by exposing insulin to an elevated temperature which will result in unfolding of the insulin (such as up to 70° C.). In embodiments, it may be heated up to from 50 to 69° C., such as up to 50, 51, 52, 53, 54, 55, 56, 67, 68, 59, 60, 61, 62 63, 64, 65, 66, 67, 68, or 69° C. When incubated with the lyso-PS liposomes in this state, the insulin is able to intercalate into the liposomal bilayer. The liposomes can then be cooled down to room temperature (generally between 18 to 25° C., such as, 18, 19, 20, 21, 22, 23, 34 or 25° C.). The pH range can be from 3 to 8. The present liposome compositions can be stored at room temperature in the freeze dried state for several months or in liquid or reconstituted state for up to 48 hrs, in the freezer for months, and refrigerated conditions in solid state for months and in liquid state for weeks.

In an embodiment, the association of insulin to liposomes can be made in citrate buffer or acidic condition at about pH 5.0 and incubated at 63° C. for 30 min. This approach yields much higher association efficiency compared to procedure involving Tris buffer at pH 7.0 and incubated at 37° C. for 30 min. Combination of low pH and higher incubation temperature promote alteration of conformation that appear important for loading. In an association study, 50 μg of insulin was used and an average of 87% was associated. Therefore the amount of insulin was about 43.5 μg per formulation associated with particle. In embodiments, the association may be at least 50%, at least 60%, at least 70%, at least 80% or at least 90%. In embodiments, the association may be from 80 to 99%, 75 to 99%, 75 to 95%, or 80 to 95%. In embodiments, the association may be from 80, 82, 84, 85, 86, 87, 88, 89, 90, 91, 92, 93, 94, 95, 96, 97, 98, 99 or 100%.

This results in high loading efficiency. Insulin can be loaded on to the lysoPS-liposomes at molar ratios of insulin to lipid from 1:100 to 1:10,000 (and all ratios therebetween). In embodiments, the ratio may be 1:500, 1:1,000, 1:2,500, 1:5,000, 1:7,500 or 1:10,000 and all ratios and ranges between these ratios.

In an aspect, the present disclosure provides compositions comprising liposomes complexed to insulin. For example, the composition may comprise a plurality of liposomes described herein in a suitable carrier. A suitable carrier may be a buffer or other pharmaceutical carriers or additives, excipients, stabilizers, or a combination thereof. For example, the liposomes may be formulated in sugars, starches, cetyl alcohol, cellulose, powdered tragacanth, malt, gelatin, talc, oils, glycols, glycerol monooleate, polyols, polyethylene glycol, ethyl alcohol, additional emulsifiers and the like. Examples of pharmaceutically acceptable carriers, excipients, and stabilizers can be found in *Remington: The Science and Practice of Pharmacy* (2005) 21st Edition, Philadelphia, PA. Lippincott Williams & Wilkins.

The present compositions can be formulated for oral delivery. The composition may be directly delivered to the desired location in the gastrointestinal tract using gavage. Or they can be formulated in the form of liquid, suspensions, tablets (including enteric coated tablets), gels, capsules, powder or any other form that can be ingested. Formulations can include pharmaceutical carriers known to be used for oral formulations. The formulations can be pediatric formulations, which can include various flavors and the like. The compositions may alternatively be delivered by any standard route such as intravenous, intramuscular, intraperitoneal, mucosal, cutaneous, subcutaneous, transdermal, intradermal, oral, and the like.

The size of the liposomes comprising PC and lyso-PS may be from about 50-150 nm. In an embodiment, about 90% of the liposomes are within a range of 50 to 150 nm. In an embodiment, where PC:lyso-PS (PS is 18:1) was used at a molar ratio of 70:30, the size distribution of the particles was found to be: 99% less than 250 nm, 90% less than 160 nm, 75% less than 125 nm, 50% less than 100 nm, 25% less than 70 nm. The mean diameter of the particles can be from 90 to 120 nm. For example, the mean diameter can be from 95 to 110 nm, such as, for example, about 106 nm. The size of the liposomes is for a population that was extruded six times through a 0.2 micron filter. When a PC:PS (double chain, 18:1) was similarly extruded six times through a 0.2 micron filter, the size distribution was: 99% less than 450 nm, 90% less than 280 nm, 75% less than 210 nm, 50% less than 160 nm, and 25% less than 115 nm. When a PC:PS (double chain, 16:0) was similarly extruded six times through a 0.2 micron filter, the size distribution was: 99% less than 310 nm, 90% less than 260 nm, 75% less than 240 nm, 50% less than 215 nm, and 25% less than 200 nm.

The insulin may be an insulin, such as, proinsulin, insulin lispro, insulin aspart, regular insulin, insulin glargine, insulin zinc, human insulin zinc extended, isophane insulin, human buffered regular insulin, insulin glulisine, recombinant human regular insulin, recombinant human insulin isophane, combinations thereof. The term "insulin" as used herein is intended to cover all of these forms of insulin.

The insulin liposomes of the present disclosure may be administered such that the dose of insulin is commensurate with the dosage standard in the industry. This can be determined and adjusted by a person skilled in the art, such as a clinician. For example, about 0.1 unit/kg/day to 1.0 unit/kg/day may be administered. 1 unit of insulin is about 0.0347 mg human insulin. (WHO/BS/10.2143—Working document QAS/10.381, 2010).

In addition to, or alternatively, other antigens, such as, non-specific islet cell antigens, glutamic acid decarboxylase 65 GAD 65, insulinoma antigen, heat shock protein, islet specific glucose 6 phosphate catalytic subunit related protein, imogen 38, zinc transporter 8, pancreatic duodeneal homeobox factor 1, chromogranin A, islet amyloid polypeptide, may be used.

The compositions may be administered to an individual who has diabetes, prediabetes, or who is at risk of developing diabetes.

The term "diabetes" is used interchangeably with diabetes mellitus and encompasses Type 1 Diabetes, both autoimmune and idiopathic, and Type 2 diabetes. The World Health Organization defines the diagnostic value of fasting plasma glucose concentration to 7.0 mmol/l (126 mg/dl) and above for Diabetes Mellitus (whole blood 6.1 mmol/l or 110 mg/dl), or 2-hour glucose level ≥11.1 mmol/L (≥200 mg/dL). Other values suggestive of or indicating high risk for Diabetes Mellitus include elevated arterial pressure ≥140/90 mm Hg; elevated plasma triglycerides (≥1.7 mmol/L; 150 mg/dL) and/or low HDL-cholesterol (<0.9 mmol/L, 35 mg/dl for men; <1.0 mmol/L, 39 mg/dL women); central obesity (males: waist to hip ratio >0.90; females: waist to hip ratio>0.85) and/or body mass index exceeding 30 kg/m$^2$; microalbuminuria, where the urinary albumin excretion rate ≥20 micro g/min or albumin:creatinine ratio ≥30 mg/g).

A "pre-diabetic condition" or reference to a "prediabetic" individual refers to a metabolic state that is intermediate between normal glucose homeostasis, metabolism, and states seen in frank Diabetes Mellitus. Pre-diabetic conditions include, without limitation, Metabolic Syndrome (also known as "Syndrome X"), Impaired Glucose Tolerance (IGT), and Impaired Fasting Glycemia (IFG). IGT refers to post-prandial abnormalities of glucose regulation, while IFG refers to abnormalities that are measured in a fasting state. T1D prediabetic condition as known in the art may also be characterized by the presence of one or more autoantibodies associated with T1D, and blood glucose levels or HbA1c levels that are higher than normal but are not high enough according to standard of care recommendations to require administration of insulin or an insulin analog.

Impaired glucose tolerance (IGT) is defined as having a blood glucose level that is higher than normal, but not high enough to be classified as Diabetes Mellitus. A subject with IGT will have two-hour glucose levels of 140 to 199 mg/dL (7.8 to 11.0 mmol) on the 75 g oral glucose tolerance test. These glucose levels are above normal but below the level that is diagnostic for Diabetes. Subjects with impaired glucose tolerance or impaired fasting glucose have a significant risk of developing Diabetes.

Impaired fasting glycemia (IFG) is defined as a fasting plasma glucose concentration of 6.1 mmol/L (100 mg/dL) or greater (whole blood 5.6 mmol/L; 100 mg/dL), but less than 7.0 mmol/L (126 mg/dL) (whole blood 6.1 mmol/L; 110 mg/dL).

Metabolic Syndrome according to National Cholesterol Education Program (NCEP) criteria are defined as having at least three of the following: blood pressure ≥130/85 mm Hg; fasting plasma glucose ≥6.1 mmol/L; waist circumference >102 cm (men) or >88 cm (women); triglycerides ≥1.7 mmol/L; and HDL cholesterol <1.0 mmol/L (men) or 1.3 mmol/L (women).

The present compositions may be administered to subject, which may be a mammal. The mammal can be a human, domesticated animals or pets, farm animals, non-human primates and the like. Examples include dog, cat, horse, or cow, but are not limited to these examples. A subject can be male or female of any age. A subject can be one who has been previously diagnosed with or identified as suffering from or having T1D, one or more complications related to T1D, or a pre-diabetic condition, and may have already undergone treatment for the T1D, the one or more complications related to T1D, or the pre-diabetic condition. A subject can also be one who is not suffering from T1D or a pre-diabetic condition. A subject may be one who has IGT or IFG. Alternatively, a subject can also be one who has not been previously diagnosed as having T1D, one or more complications related to T1D, or a pre-diabetic condition. A subject can be one who exhibits one or more risk factors for T1D, complications related to T1D, or a pre-diabetic condition, or a subject who does not exhibit T1D risk factors, or a subject who is asymptomatic for T1D, one or more T1D -related complications, or a pre-diabetic condition.

In an embodiment, the present lysoPS-insulin liposome compositions are administered to the subject for delaying the onset of T1D. The subject may be in the prediabetic stage of T1D, or may be a subject who is at risk of becoming a prediabetic. The subject may have IGT or IFG. In an embodiment, the compositions are administered to a subject before the subject has developed hyperglycemia. In another embodiment of the invention, the subject has developed hyperglycemia when treatment is initiated.

In an embodiment, the present lysoPS-insulin liposome compositions are administered to the subject who is predisposed for T1D.

In an embodiment, the present lysoPS-insulin liposome compositions can be administered to treat a subject who is beyond the prediabetic stage and may be considered to have T1D. The treatment may result in arresting the progression of the disease, reversing one or more symptoms of the disease, or preventing or delaying development of complications associated with T1D.

The present compositions may be administered as needed. For example, the present composition may be administered prior to a meal or an expected rise in blood glucose. It may be administered multiple times a day on a routine basis. It may be administered in single or multiple doses throughout the day for a few days, weeks, months or as a maintenance therapy for years. It may be administered using any suitable delivery device.

Some examples of specific embodiments are provided below.

A composition comprising or consisting essentially of a plurality of liposomes, wherein the insulin is intercalated in the liposome bilayer and wherein the liposomes comprise phosphatidylcholine (PC) and lyso-phosphatidylserine (lyso-PS), wherein the ratio of PC to lyso-PS is from 90:10 to 60:40. The acyl chain of the lyso-PS can be oleic acid (18:1). The ratio of PC to lyso-PS can be from 85:15 to 70:30. The PC may be present as dimyristoyl-sn-glycero-3 phosphatidylcholine (DMPC). The size of the liposomes can be from 80 to 150 nm (e.g., for 90% of the population). The zeta potential of the liposomes can be from −8 to −40. The PC and lyso-PS may be the only phospholipids present in the bilayer of the liposome.

A method for delaying the onset, suppressing, treating, preventing, or alleviating the symptoms of type 1 diabetes, or reversing one or more symptoms of T1D by administering to an individual, who is in need a composition comprising or consisting essentially of liposomes complexed to insulin (insulin being intercalated in the bilayer), wherein the liposomes comprise PC:lyso-PS in a ratio of 85:15 to 70:30. All of PC can be is dimyristoyl-sn-glycero-3 phosphatidylcholine (DMPC). The acyl chain in lyso-PS can be oleic acid. The liposomes may not have any other protein (other than insulin) intercalated in the bilayer. The regimen for administration can continue as long as needed to avoid or treat or prevent the symptoms of type 1 diabetes. Administrations can be carried out multiple times a day, daily, weekly, monthly or as recommended by a treating clinician.

The following examples are further embodiments are non-restrictive illustrations of the present disclosure.

EXAMPLE 1

A method of delaying the onset of type 1 diabetes comprising administering to an individual in need of treatment a composition comprising liposomes which comprise phosphatidylcholine (PC) and lysophosphatidylserine (lyso-PS), wherein the ratio of PC to lyso-PS is from 90:10 to 60:40, and insulin intercalated in the liposomal bilayer.

EXAMPLE 2

A method for preventing, treating, suppressing type 1 diabetes, or reversing one or more symptoms of T1D comprising administering to an individual in need of treatment a composition comprising liposomes which comprise phosphatidylcholine (PC) and lysophosphatidylserine (lyso-PS), wherein the ratio of PC to lyso-PS is from 90:10 to 60:40, and insulin intercalated in the liposomal bilayer.

The method of Examples 1 or 2, wherein the acyl chain of the lyso-PS is oleic acid.

The method of Example 1 or Example 2, wherein the ratio of PC to lyso-PS is from 85:15 to 70:30.

The method of Example 1 or Example 2, wherein the PC is present as dimyristoyl-sn-glycero-3 phosphatidylcholine (DMPC).

The method of Example 1 or Example 2, wherein PC and lyso-PS are the only phospholipids present in the bilayer of the liposome.

The method of Example 1, wherein the individual is a prediabetic.

A method for regulating blood glucose levels comprising administering to an individual in need of treatment a composition comprising liposomes which comprise phosphatidylcholine (PC) and lysophosphatidylserine (lyso-PS), wherein the ratio of PC to lyso-PS is from 90:10 to 60:40, and insulin intercalated in the liposomal bilayer.

A method of short term lowering of blood glucose comprising administering to an individual who is exhibiting higher than normal glucose levels and is in need of exogenous invention a composition comprising liposomes which comprise phosphatidylcholine (PC) and lysophosphatidylserine (lyso-PS), wherein the ratio of PC to lyso-PS is from 90:10 to 60:40, and insulin intercalated in the liposomal bilayer.

The following example is further provided for illustrative purposes and not intended to be limiting.

EXAMPLE 1

Type 1 Diabetes is a complex autoimmune disease involving cell-mediated immunity as well as humoral immunity. The present results showed insulin associated with LysoPS has a high association efficiency while conserving protein conformation. Using NOD mice, we showed this formulation delayed type 1 diabetes onset and decreased incidence of type 1 diabetes. Lower anti-insulin antibody titer with expansion of regulatory T cells was observed. Therefore, we conclude that this innovative lipid nanoparticle immunotherapy can be used as an alternative treatment for Type 1 diabetes during prediabetes stage.

Abbreviations: Circular dichroism, CD; Dynamic light scattering, DLS; Dimyrisotylphosphatidylcholine, DMPC; Lysophosphatidylserine, LysoPS; Insulin complexed with Lyso-PS nanoparticle, LysoPS-insulin; mesenteric lymph nodes, MLNs; non-obese diabetic, NOD; Phosphatidylserine, PS; Polydispersity index, PDI; Standard deviation, SD; Standard error of the mean, SEM.

Materials and Methods:

Dimyrisotylphosphatidylcholine (DMPC) and 18:1 Lyso-phospho-L-serine (Lyso-PS) were purchased from Avanti Polar Lipids (Alabaster, AL). Full length recombinant human insulin was purchased from SAFCBioscience (Lenexa, Kansas). All salts and solvent were obtained from Fisher Scientific (Fairlawn, NJ), Sigma Aldrich (St. Louis, MO) or J.T. Baker Chemical (Phillipsburg, NJ). Sephadex-G-75 beads, horseradish peroxidase-conjugated goat anti-mouse IgG antibody and 3,3',5,5'-tetramethylbenzidine substrate (TMB) were purchased from Sigma (St. Louis, MO). Micro-BCA kit was purchased from Thermo Scientific (Rockford, IL). Endosafe Endochrome-K® Kit was purchased from Charles River Laboratories (Charleston, SC). NUNC MaxiSorp 96 well plates, 10% formalin and 200 proof ethanol were purchased from Thermo Scientific (Waltham, MA). Regulatory T cell detection kit was purchased from Miltenyi biotec (Germany). Glucometer and Glucose strips was purchased from Contour Next (Parsippany, NJ). Polycarbonate membrane was purchased from GVS Filter Technology (Sanford, ME). RMPI 1640 with L-glutamine was purchased from Corning cellgro (Manassas, VA).

Female NOD/ShiLtj were purchased from Jackson Laboratory at the age of 8 weeks and were housed in a 12 h dark/light cycle with food and water bottle. All mice were fasted for 6 hours before weekly blood glucose measurement and their health condition was monitored daily. Weight was measured twice a week for monitoring clinical condition. All animal experiments were conducted under approval and followed the guidelines of the Institutional Animal Care and Use Committee (IACUC) at the University at Buffalo, The State University of New York.

Preparation of LysoPS-Insulin Nanoparticle (LysoPS-Insulin)

LysoPS lipid nanoparticles were prepared at a molar ratio of 30:70 of LysoPS to DMPC in chloroform. LysoPS lipid nanoparticles were prepared using thin film, dehydration and rehydration methods. Chloroform solvent was removed by rotary evaporation to form a thin lipid film on the bottom of a test tube and rehydrated in 1 ml of sterile 5 mM citrate buffer at pH 5.0. LysoPS lipid nanoparticles were sized by extruding them through a polycarbonate membrane of 200 nm pore size using high-pressure nitrogen extrusion. The mean diameter of lipid nanoparticles was confirmed by dynamic light scattering (Nicomp 380 Particle Sizer, Particle Sizing System, Port Richey, Florida). Lipid concentration was determined using phosphate assay. The molar ratio of insulin to lipid used was 1:100 for biophysical characterization and 1:1000 for the formulation orally administered to NOD/ShiLtj mice. LysoPS lipid nanoparticles were associated with insulin using a trigger-loading mechanism by incubating insulin with LysoPS lipid nanoparticles at 63° C. for 30 min to promote insulin association. They can be brought down to room temp. Free insulin need not be removed but may be removed using Sephadex column.

Biophysical Characterization of LysoPS-Insulin Lipid Nanoparticle

Characterization of LysoPS-Insulin Lipid Nanoparticles

LysoPS-insulin nanoparticle complexes and Lyso-PS nanoparticles alone were characterized by measuring size and zeta potential using dynamic light scattering technique with a laser set at 640 nm at a concentration of 1 μmol/ml. Both measurements were performed at 25° C. Particle sizing was performed at a 90° angle using NNLS mode for analyzing size distribution. Zeta potential was calculated using the Smoluchowski equation and ran in 30 cycles. The reported results (mean±SD) are the average of three independent experiments.

Association Efficiency Using Gel Filtration Chromatography

To optimize the association of insulin with LysoPS nanoparticles, recombinant human insulin and LysoPS nanoparticles were made in two formulations both in a 1:100 protein to lipid ratio. The first in 25 mM Tris buffer at pH 7.0 and incubated at 37° C. for 30 min and the second in 5 mM citrate buffer at pH 5.0 and incubated at 63° C. for 30 min for association. Insulin concentration was 500 m/ml to allow detection using the Micro-BCA protein assay. 100 μl of formulation, either insulin alone, LysoPS lipid nanoparticle alone or LysoPS-insulin lipid nanoparticle group, were loaded onto Sephadex G-75 column rehydrated with 25 mM Tris buffer or 5 mM citrate buffer with 0.15 M of NaCl. The experiment was performed 3 times to validate the results. To determine the fractions in which insulin-LysoPS lipid nanoparticle elute from the column, lipid nanoparticles were prepared containing 0.1 mol % rhodamine-PE conjugated to the lipid nanoparticle during production. Rhodamine labeled nanoparticles were detected using spectrofluorometer at the excitation wavelength 560 nm with emission of 585 nm. To determine association efficiency, 50 fractions of 0.55 ml, were collected individually and the insulin concentration in each fraction was determined using Micro-BCA protein assay. LysoPS alone were run to correct for the interference in the Micro-BCA in LysoPS-insulin group. The association efficiency of LysoPS-insulin nanoparticle was calculated using the following equation.

$$\text{Insulin association efficiency} = \frac{\text{Insulin alone} - Lyso\text{-}PS \text{ insulin}}{\text{Insulin alone}}$$

Circular Dichroism Studies

To determine the stability of insulin and LysoPS-insulin lipid nanoparticles, Circular Dichroism (CD) spectra were obtained using JASCO-815 CD spectrometer fitted with a Peltier 300 RTS unit for temperature dependent studies. The far UV spectra for secondary structural analysis was acquired at the wavelength range of 204 nm to 260 nm with 200 m/ml concentrations being measured in 1 mm path length quartz cuvette. Acquisition parameters include a scanning speed of 20 nm per minute, a response time of 2 second. A far-UV spectra was first obtained in 5 mM citrate buffer at the volume of 250 μL to capture the background of light scattering. Then far-UV spectra were obtained for each experimental group; insulin alone at 20° C., 63° C., LysoPS lipid nanoparticle alone, or LysoPS-insulin lipid nanoparticles. CD spectra of citrate buffer alone was measured and used to subtract background scattering; CD spectra of LysoPS lipid nanoparticles alone were used to subtract scattering from LysoPS lipid nanoparticles associated with insulin.

Steady State Fluorescence Studies

Steady-state emission and excitation spectra were acquired using a PTI fluorometer (Photon Technology International, Lawrenceville, NJ) equipped with a Peltier unit. Tertiary structure of LysoPS-insulin nanoparticles was measured in order to verify its stability. All samples; 5 mM citrate buffer, insulin alone, LysoPS lipid nanoparticles alone and insulin associated LysoPS lipid nanoparticles were prepared in 0.8 ml quantities and the concentration of insulin used was 10 ug/ml. Each sample was placed into a 1 cm path length quartz cuvette, excited at 265 nm and the emission was monitored in the wavelength range of 300 nm to 400 nm. The excitation and emission slits were both set at 4 nm. Excitation wavelength at 265 nm was used to reduce interference of Raman bands and Rayleigh scattering near the peak emission of insulin.

In Vivo Study

Determination of Disease Progression:

Human insulin sequence is highly homologous with mouse insulin; both human insulin and mouse insulin contains identical autoreactive insulin B chain 9-23aa (Yang et al., PNAS, Oct. 14, 2014, 111(41)14840-14845) which is able to recognize and induce immune reaction in NOD mice model. Therefore, recombinant human insulin was used. NOD/ShiLtj mice were fed 1 μg of insulin via oral gavage with or without LysoPS lipid nanoparticles in a protein to lipid molar ratio of 1:1000.

Each group consisted of 8 mice except in LysoPS alone group with 7 mice for the study, where 1 mouse had to be excluded. Mice were treated through oral gavage weekly starting at 12 weeks of age and continued until mice reached 30 weeks of age. Saphenous vein blood collection was performed weekly and plasma was collected to measure anti-insulin antibodies as well as to monitor blood glucose levels. 1 μl of serum plasma was used for monitoring glucose level using a handheld Contour next one glucometer from Bayer. Mice body weights were also measured twice a week as a way to monitor disease progression in the mice. Mice with more than 10% weight lost were given wet chow daily, 15% weight loss were given 1 mL normal saline subcutaneously and mice with more than 20% weight loss were euthanized. At the conclusion of the study, mice were sacrificed by cardiac puncture and plasma, spleens, and pancreas were collected for analysis.

Determination of Anti-Insulin Antibodies:

Total anti-insulin autoantibody titers were determined by Indirect ELISA. A 96-well Maxisorb plate was coated with 50 μL of 5 μg/mL of insulin in sodium bicarbonate buffer at pH 9.6 overnight. The plate was washed in PBS buffer containing 0.05% Tween20 at pH 7.4 six times using an automated plate washer. Then, the plate was blocked with 300 μl of PBS containing 0.1% v/v Bovine serum albumin (BSA) and incubated at 37° C. for 2 hours to avoid non-specific binding. Samples were serially diluted in three-fold dilution before added onto the plates. The plates were washed again and 100 μl of the diluted plasma samples were added to the plate in duplicate. Three naive control samples were used from untreated NOD mice, each control plasma was diluted until the baseline of detection is achieved. Controls were added to the plate in triplicate and all of the samples incubated at 37° C. for 1 hour and washed again. Then 100 μL of a 1:5000 dilution of Goat anti-mouse immunoglobulin-peroxidase in PBS buffer containing 0.1% BSA is added to each well, and is incubated for one hour at room temperature (RT). The plate was washed again and 100 μL of 3,3',5,5'-tetramethylbenzidine was added to each well for twenty minutes and incubated at RT in the dark. The reaction was stopped by the addition of 2N sulfuric acid to each well. Absorbance of the plate was read at 450 nm using a Spectramax plate reader. Total antibody titers were determined from weekly blood samples and compared among the treatment groups.

CD4+FoxP3+ Regulatory T-Cells, CD4+ and CD8 T Cells Regulation:

Spleens were isolated and homogenized from the NOD mice that are given lysoPS-insulin orally at the end of the study. To determine population of regulatory T cells, we captured CD4+, FoxP3+ cell surface marker as regulatory T cells population, CD4 marker as general CD4+ subset T cells population and CD8 as general CD8+ T cells subset population from TCR-β expressing T cells population using flow cytometry. CD4+ antibody is conjugated with FITC, FoxP3+ antibody is conjugated with PE and CD8 is conjugated with APC. 4 mice from each group were scarified except in the LysoPS treatment group where 8 mice was included in the group. Lymphocytes isolated from spleen and were treated with RBC lysis buffer for 5 min and lymphocytes population were counted using BC-2800 Vet hemocytometer analyzer from Mindray. For staining procedure, $2\times10^6$ of lymphocytes were resuspended and fluorescently labeled with anti-TCR-β-APC-Vio 700, anti-CD4-FITC, anti-FOXP3-PE, and anti-CD8-APC antibodies using Regulatory T cells detection kit and anti-CD8+ antibody from Miltenyi Biotec following recommended protocol for cell surface staining and intracellular staining. Single stained cells were used for compensation and unstained cells used to determine background fluorescence and adjust voltage and negative gate. CD4+ isotype is used as control to determine non-specific binding of antibody but not in FOXP3 isotype. Intracellular staining with control isotype may have non-specific binding of both antibodies and fluorophore with intracellular component. For CD4+ and CD8+ T cells population, both populations are double gated using gating with CD4+ alone and CD8+ alone from TCR-β expressing population. Each sample were counted at 10,000 events per samples using Miltenyi Analyzer 10 Flow cytometer. In addition, other type of regulatory cells, such as LAP+ Tergs are also measured.

Histological Assessment

Diabetes is defined by the infiltration of T cells and results in self-destruction of β cells at the islets of Langerhans. To determine if LysoPS-insulin nanoparticles can induce tolerance at the β cells and maintain the healthy structure of β cells, we investigated the histology of pancreas. 5 mm thick slices of the pancreas were isolated from NOD mice with 3 mice from each sample group and were fixed with 50 ml of 10% Neutral Buffered Formalin overnight. Pancreas specimens were washed three times in cold PBS to remove excessive formalin for 1 hour and stored in 70% ethanol for 24 hours prior to tissue sectioning, paraffin embedding and staining with Hematoxylin and Eosin. Images of the pancreas were captured and pancreas morphology was analyzed using confocal microscopy (a Zeiss Axiovert 200M microscope) with 200× magnification.

Statistical Analysis

The statistical analysis performed using Prism 8.2 software (GraphPad software Inc, San Diego, CA, USA). Size distribution and zeta potential comparison performed using student paired t test with $P<0.05$ consider as significant. Diabetes incidences were analyzed using a Kaplan-Meier test (log-rank Mantel Cox test). The analysis of variance was measured using Kruskal-Wallis test with Dunn's multiple comparison's test for antibody titer and T cells population.

Results

Association Efficiency of LysoPS-Insulin Lipid Nanoparticle

To assess insulin association efficiency, insulin and LysoPS nanoparticle mixture were trigger loaded at 37° C., pH7.0, in Tris buffer or at 63° C., pH5.0, in citrate buffer. Clear separation is achieved by size chromatography using a sephadex G-75 column. Sephadex gel is a mixture of cross-linked dextran beads that allows formation of a three-dimension network used for size exclusion filtration with different size of porosity. LysoPS-insulin nanoparticles display a larger molecular size and elute at earlier fractions in the column than unassociated insulin (FIG. 1). Our data showed LysoPS-insulin associated at 37° C., pH7.0, in Tris buffer has an association efficiency of 9.53%. When association was carried out at higher temperatures and in acidic conditions, increased association efficiency, was observed. It is considered that high temperature may allow exposure of hydrophobic domains of insulin and induce phase transition of LysoPS lipid nanoparticles that expose hydrophobic regions allowing association of insulin protein. As a result, it was found that incubation of insulin at 63° C., pH5.0, in citrate buffer is the optimal condition for achieving high association efficiency of protein with lipid particle. The following conditions have been investigated: Tris Buffer, pH7.0 63 C, resulting in an association 12%, and PBS at pH 5.0 at 37 C, resulting in association 15%, PBS at 5.0 at 63 C, resulting in an association 55%. But PBS does not have a good buffer capacity at pH 5.0, therefore, switched to citrate buffer that gave the highest association efficiency (See FIG. 1, Tables 1 and 2). A combination of citrate buffer, slightly lower than neutral pH and elevated temperature was found to be ideal for association. Any other buffer that may have a buffering capacity that is slightly lower than neutral may be used (e.g., Histidine buffer). In an embodiment, the association can be made in citrate buffer or acidic condition at about pH 5.0 and incubated at 63° C. for 30 min. This approach yields much higher association efficiency compared to procedure involving Tris buffer at pH 7.0 and incubated at 37 C for 30 min. Combination of low pH and higher incubation temperature promote alteration of conformation that are critical for loading.

Dynamic Light Scattering (DLS)

To demonstrate stability of LysoPS-insulin after trigger loaded insulin into LysoPS nanoparticles, both size and zeta potential were measured using DLS. The particle size of unloaded LysoPS alone was 61.1±1.96 nm (mean±SD) and increased to 93.55±20.24 nm after association. The polydispersity index (PDI) of LysoPS lipid nanoparticles alone had an average of 0.18 but when insulin was loaded into the LysoPS lipid nanoparticles, the PDI increased to 0.32. A small increase in size is due to insulin is intercalated within the lipid bilayer. No large increase in size was observed, indicating that no vesicle fusion. Zeta potential can be used to determine the surface charge of the LysoPS nanoparticle before and after association with insulin. Results showed that zeta potential was not significantly altered after insulin loading with a net negative charge of −24.62±4.88 mV in LysoPS alone and −24.86 mV±0.38 for insulin-associated lipid nanoparticle. This data supports insulin association with LysoPS lipid nanoparticles did not disrupt the serine head group and phosphorus backbone of the lipid, suggesting insulin loading does not disrupt LysoPS nanoparticles.

Circular Dichroism Study

Apart from liposomal stability, insulin stability was investigated before and after association with LysoPS nanoparticle. Insulin stability was investigated by monitoring secondary structure of the protein using Circular Dichroism (CD) with Far-UV CD spectrum. Circular dichroism measures unequal absorption of left-handed and right-handed circularly polarized light by aromatic residues and cysteine in protein molecules. Changes in CD signal imply changes in secondary structure and correlated to the changes in stability. Free insulin showed two bands one at 208 nm and the other at 220 nm consistent with alpha+beta protein. Heating to 63° C. in acidic conditions the intensity of negative band at 208 nm increased suggesting loss of alpha structure and possibly a shift in equilibrium towards monomeric insulin from multimeric configuration (FIG. 2). Our data showed LysoPS-insulin nanoparticles showed significant change in intensity and the intensity of the 208 nm is more intense than 220 nm, possibly due to formation of more monomeric species upon association with lysoPS particle.

State Steady Fluorescence Emission

Steady-state fluorescence spectrometry is a rapid and sensitive technique to study the tertiary structure of protein. Intrinsic protein fluorescence can be generally detected using three amino acids; tryptophan, tyrosine and phenylalanine. Since insulin does not contain tryptophan, tyrosine plays a more important role in fluorescence characterization. To characterize the tertiary structural changes of insulin following association with LysoPS, free and lysoPS associated insulin was monitored using fluorescence. The excitation was set at 265 nm. Insulin alone and heated insulin to 63 C alone were added as control. Our data showed insulin alone and LysoPS-insulin nanoparticles displayed a similar emission peaks at 304 nm and in comparison, no significant shift of peak intensity was shown (FIG. 3). A single peak intensity at 304 m demonstrated tyrosine is the dominant amino acid in insulin and tryptophan is not present. Due to similarity fluorescence emission peaks in both insulin alone and LysoPS-insulin, our data demonstrated LysoPS lipid nanoparticle do not alter the tertiary structure of insulin upon association. In addition to fluorescence emission, fluorescence excitation spectrum provided additional information relating to insulin association. The fluorescence excitation spectra showed that insulin alone has two excitations peaks one at 228 nm and the other at 279 nm and LysoPS-insulin nanoparticle also showed two excitation peaks at 228 nm and 273 nm. The excitation peak at 228 nm is considered to represent excitation in the far UV region and brings the molecules to higher energy states 1Ba and 1Bb while excitation around 270 nm excite molecules to higher energy at 1La and 1Lb state near-UV region. As shown in FIG. 3*b*, Insulin alone has a higher absorbance at an excitation wavelength of 279 nm while Lyso-PS insulin has a lower absorbance and blue shifted to a higher energy wavelength at 273 nm. The lower excitation wavelength and absorbance showed dominance of 1La state excitation in the presence of non-polar liposomal environment compared to Insulin alone. Further, more monomeric insulin species is formed. Therefore, the high excitation and reduction in absorbance intensity confirmed that insulin was associated with non-polar LysoPS lipid nanoparticles possibly in predominantly in a monomeric form.

Use of LysoPS Nanoparticles Delayed T1D Incidence

To demonstrate the effect of lysoPS liposomes on diabetes, NOD mice were used. The NOD mice received weekly low dose of LysoPS-insulin nanoparticles and were monitored beginning on week 12, and continued to 30 weeks. Female NOD mice were used for this study because NOD mice models developed critical diabetes features that correlated with human disease and female mice generally develop higher incidence of diabetes between 60% and 90% compared to males. Mice were fasted for 6 hours to measure blood glucose levels and mice were considered diabetic when blood glucose level was consistently high after two consecutive positive readings (>250 mg/dl). The protein free LysoPS alone group first developed diabetes at the age of week 14 and resulted in a final diabetes incidence of 42.8%. Animals in both control groups, citrate buffer and insulin alone treated group, first developed diabetes incidence at the week of 15 and have a final diabetes incidence of 62.5%. LysoPS-insulin treatment group first developed diabetes incidence at the week of 27 and showed a significantly lower final diabetes incidence with 12.5% compared to buffer and free insulin treatment (FIG. 4). Body weight was also monitored for mice in each treatment group (FIG. 5) and body weight was significantly higher in Lyso-PS insulin treated animals, showing normal growth and did not experience physical symptoms of diabetes. Therefore, LysoPS-delayed onset of diabetes event in NOD mice.

LysoPS Insulin Liposomes Reduce Antibody Development

To test the effect of LysoPS-insulin on antibody titer, the following studies were carried out. Anti-insulin antibody titers were evaluated using indirect ELISA as described in methods section and blood samples were collected weekly from NOD mice. Anti-insulin antibody levels were analyzed beginning at week 12 of their age (FIG. 6), mice received treatment from each group displayed similar anti-insulin autoantibody level at week 12 were with 798.2 unit±287.1 in buffer treated animals, 553 unit±95.64 in the insulin group, 765.2 unit±96.69 in LysoPS alone group and 1139 unit±129.4 in LysoPS-insulin treated group. As treatment continued, mice began to show increase in titers; titer levels in LysoPS-insulin were significantly lower compared with insulin alone and LysoPS alone, with titers at 434.3 unit±58.66, 949 unit±117 and 1269 unit±110.3 respectively. At week 23 antibody titers in LysoPS-insulin treated group there was no increase in mean titers with antibody titers at 600.9 unit±53.93 while antibody titers in untreated controls continuous to rise. Buffer treated animals had antibody titers 1408 unit±261.8 and insulin alone treated animals had antibody titers 1441unit ±303.7, showing antibody titer developments were significantly higher in the untreated control group. (FIG. 6) As expected, increased anti-insulin antibodies titer correlated with increase in diabetes incidence in control groups while mice in LysoPS-insulin group remains stable. Antibody titers were analyzed at the conclusion of the study and showed that antibody titers were found to be lower for LysoPS-insulin treated group compared to other treatment groups.

Effects on T Cells Subpopulation

To investigate the population of regulatory T cells (Tregs) in each treatment group, cells were isolated from the spleen and stained with T cell receptor marker, CD4+ T cell marker, CD8+ T cells marker and Foxp3+ marker. Tregs were defined as T cells expressing CD4+ and FOXP3+ phenotype in this study. For the gating technique, cellular debris and doublet cell is excluded by examining side scatter (SSC-W) and forward scatter (FCS-A), resulting in a 65.3% population (FIG. 7*a*). Then a second singlet cells selection is performed through FSA-A versus FSC-H and using T-cell receptor conjugated with fluorophore to isolate T cells population out of the total population and the result retained 27.7% of cells. Sub-population of T cells were identified through staining with CD4-FITC and CD8-APC antibody to determine the population. Regulatory T cell population is stained with CD4-FITC and FOXP3-PE out of the total T cell population. In order to reduce the overlap between detection probes, compensation was performed. With respect to Tregs population, LysoPS-insulin group had a mean count of 0.7957±0.3717 million of T lymphocytes whereas 0.2745±0.1753 million of T lymphocytes in buffer treated group was observed. The insulin alone group showed 0.5331±0.08049 million counts and 0.4262±0.09158 million was counted for LysoPS alone treatment group. Population of regulatory T cell in LysoPS-insulin treatment group were statistically higher compared to buffer treated mice (p=≥0.05). Expansion of CD4+ cell population revealed the following: In LysoPS-insulin group with 54.94%±1.234 of T lymphocytes compared to buffer treated 45.5%±2.302 of T lymphocytes, insulin alone treated with 48.85%±1.17 of T lymphocytes (p=0.0061), and LysoPS alone treated with 48.47%±5.139 of T lymphocytes, was statistically significant (p=0.0012), suggesting expansion of CD4+ T cells population is result of proliferation of CD4+ T cells into tolerogenic phenotype in LysoPS-insulin group. These data suggest that the late onset of diabetes in LysoPS-insulin maybe contributed by continuous β cells disruption through cytotoxic CD8+ T cells immune response. We measured the population of CD8+ T cells in LysoPS-insulin treated group (41.13%±2.668) compared with buffer (49.93%±5.271), insulin alone (43.45%±4.279) and LysoPS alone (48.87±8.039) treated control group, found that CD8+ T cells in LysoPS-insulin group is lower than other treatment group (See FIG. 7*b*).

Pancreas Morphology

Histology of the pancreas from all groups were evaluated at the end of the study. All of the mice in the buffer group showed decreased mass of islets cells and irregular cell structure showing cell necrosis and tissue destruction. Pancreatic tissue was isolated and stained with Haemotoxylin and Eosin to visualize pancreas morphology after treatments. Morphology of islet cells in NOD mice that received LysoPS-insulin showed improved islet cell condition, maintain regular cellular structure with higher cellular mass and fewer mononuclear cell infiltration, in comparison with control groups; buffer, insulin alone and LysoPS alone treated group (FIG. 8A-M). Mononuclear cell infiltration containing T cells and B cells for inflammatory immune response against β-cells, indicated an initial event of T1D and reduction in β-cell mass. In the LysoPS-insulin group however, islet cells did not observe β-cell reduction or disruption, indicating LysoPS-insulin treatment improved overall β-cell condition. Pancreas obtained from LysoPS-insulin group also displayed mononuclear cell infiltration and the data showed that LysoPS-insulin did not fully prevent leukocyte infiltration, which correlated to late development of T1D in LysoPS-insulin treated group. These data indicate that LysoPS prevents development of diabetes and protects the destruction of Beta cell islet mass thus offering a cure for T1D. Further, starting the treatment with 12 weeks old mice also showed early reversal of the diabetes.

EXAMPLE 2

In order to understand the fate of lysoPS nanoparticles after oral administration, we investigated the stability of nanoparticle in in vivo, using imaging with a fluorescence probe, indocyanine green (ICG). ICG and ICG labeled lysoPS nanoparticles were administered to Swiss Webster mice and the fate of the nanoparticle in the gut was tracked (FIG. 9). Fluorescence intensity of particle bound ICG is much higher than free ICG, therefore stability of particle can be directly measured from fluorescence imaging. At 5 min, 1 h, and 3 h post administration, mice were sacrificed and GI tracts were isolated for imaging using the FMT 2000 In Vivo Imaging System. The results showed that ICG in lysoPS lipidic nanoparticles, the fluorescence intensity achieved was much higher than naked ICG in aqueous solution. At 5 min post administration, both naked ICG and lysoPS-ICG started to travel down the small intestine. The lower fluorescence intensity observed in naked-ICG-treated animal is due to the quenching of fluorescence by low pH environment of stomach and small intestine. At 1 h post administration, substantial fluorescence was observed in the small intestine for lysoPS ICG group as the formulation started to reach the lower part of small intestine. At 3 h post administration, fluorescence intensity in lower part of intestine was observed for lysoPS and was eliminated out of the body through fecal matter. Taken together, this data indicates that oral delivery of insulin using lysoPS nanoparticles be carried out and that will survive the challenging oral route, stomach and in the gut environment.

In order to understand the PK of insulin loaded in LysoPS nanoparticles, we performed pharmacokinetic analysis of LysoPS-insulin in 3 Streptozotocin STZ-induced rats (200 g-300 g) following oral administration. Insulin concentration was measured at different time points using ELISA (Alpco bioscience). As is clear from FIG. 10, LysoPS-insulin showed a biphasic absorption, one from possibly stomach approximately peak at 15 min and the second absorption at 180 min from intestine after oral gavage. The glucose level was monitored in these animals. An increase in insulin concentration showed a concomitant drop in glucose levels.

The preceding description provides specific examples of the present invention. Those skilled in the art will recognize that routine modifications to these embodiments can be made which are intended to be within the scope of the invention.

What is claimed is:

1. A method of treating type 1 diabetes (TID) comprising orally administering to an individual in need of treatment a composition comprising liposomes which comprise phosphatidylcholine (PC) and lysophosphatidylserine (lyso-PS), and insulin, wherein the ratio of PC to lyso-PS is from 90:10 to 60:40, and at least part of the insulin is intercalated in the liposomal bilayer.

2. The method of claim 1, wherein treating comprises suppressing or reversing one or more symptoms of TID.

3. The method of claim 1, wherein treatment comprises regulating blood glucose levels.

4. The method of claim 3, wherein treatment comprises lowering of blood glucose levels to normal levels.

5. The method of claim 3, wherein treatment comprises lowering circulating anti-insulin antibody titer.

6. The method of claim 1, wherein the acyl chain of the lyso-PS is oleic acid.

7. The method of claim 1, wherein the ratio of PC to lyso-PS is from 85:15 to 70:30.

8. The method of claim 1, wherein the PC is present as dimyristoyl-sn-glycero-3 phosphatidylcholine (DMPC).

9. The method of claim 1, wherein PC and lyso-PS are the only phospholipids present in the bilayer of the liposome.

10. The method of claim 1, wherein the individual is a prediabetic.

11. The method of claim 1, wherein insulin is intercalated into the liposomal bilayer by a process comprising altering the conformation of insulin by exposing to temperatures up to 70° C., contacting with liposomes to form complexes, and allowing the complexes to cool to room temperature.

12. The method of claim 9 wherein the molar ratio of insulin to lysoPS is from 1:100 to 1:10,000.

13. A method of treating type 1 diabetes (TID) comprising cutaneously administering to an individual in need of treatment a composition comprising liposomes which comprise phosphatidylcholine (PC) and lysophosphatidylserine (lyso-PS), and insulin, wherein the ratio of PC to lyso-PS is from 90:10 to 60:40, and at least part of the insulin is intercalated in the liposomal bilayer.

* * * * *